(12) United States Patent
Lee et al.

(10) Patent No.: US 11,073,580 B2
(45) Date of Patent: Jul. 27, 2021

(54) RADIO FREQUENCY COIL AND MEDICAL IMAGING DEVICE INCLUDING SAME

(71) Applicant: INDUSTRY-ACADEMIC COOPERATION FOUNDATION, YONSEI UNIVERSITY, Seoul (KR)

(72) Inventors: Young Han Lee, Seoul (KR); Min Jung Kim, Seoul (KR); Jaemoon Yang, Seoul (KR); Jin-Suck Suh, Seoul (KR)

(73) Assignee: INDUSTRY-ACADEMIC COOPERATION FOUNDATION, YONSEI UNIVERSITY

( * ) Notice: Subject to any disclaimer, the term of this patent is extended or adjusted under 35 U.S.C. 154(b) by 58 days.

(21) Appl. No.: 16/475,228

(22) PCT Filed: Dec. 29, 2017

(86) PCT No.: PCT/KR2017/015781
§ 371 (c)(1),
(2) Date: Jul. 1, 2019

(87) PCT Pub. No.: WO2018/124834
PCT Pub. Date: Jul. 5, 2018

(65) Prior Publication Data
US 2019/0339343 A1    Nov. 7, 2019

(30) Foreign Application Priority Data

Dec. 30, 2016   (KR) .................. 10-2016-0183203

(51) Int. Cl.
*G01N 27/416*   (2006.01)
*G01R 33/34*    (2006.01)
(Continued)

(52) U.S. Cl.
CPC ........ *G01R 33/34069* (2013.01); *A61B 5/055* (2013.01); *A61B 6/502* (2013.01); *G01R 33/3415* (2013.01)

(58) Field of Classification Search
CPC ............. G01R 33/34; G01R 33/34007; G01R 33/34069; G01R 33/3415;
(Continued)

(56) References Cited

U.S. PATENT DOCUMENTS 4,816,765 A * 3/1989 Boskamp ........... G01R 33/3678
                                                    324/318
4,827,327 A * 5/1989 Miyauchi ............... H05K 1/184
                                                    257/700

(Continued)

FOREIGN PATENT DOCUMENTS

JP    2008539041 A    11/2008
JP    2013505111 A    2/2013
(Continued)

OTHER PUBLICATIONS

Aklan, Bassim et al., "Toward simultaneous PET/MR breast imaging: Systematic evaluation and integration of a radiofrequency breast coil", Medical Physics, vol. 40, No. 2, Feb. 2013.
(Continued)

*Primary Examiner* — Thang X Le
(74) *Attorney, Agent, or Firm* — Renaissance IP Law Group LLP

(57) ABSTRACT

A medical radiofrequency coil may comprise: a base substrate; and a radio coil unit having a first coil element which has a rectangular shape and is formed along an edge of the inner peripheral surface of the base substrate, and a second coil element which is formed at the inner side of the first coil element and has a shape of paired paddles connected to each other. Therefore, the present inventive concept provides a
(Continued)

radiofrequency coil, which can minimize an image distortion due to a beam-hardening artifact effect, and a medical imaging device including the same.

11 Claims, 15 Drawing Sheets

(51) Int. Cl.
*A61B 5/055* (2006.01)
*A61B 6/00* (2006.01)
*G01R 33/3415* (2006.01)

(58) Field of Classification Search
CPC ........... G01R 33/34061; G01R 33/481; G01R 33/36; G01R 33/3635; G01R 33/3642; G01R 33/48; G01R 33/4818; G01R 33/4824; G01R 33/446; G01R 33/4835; G01R 33/4828; G01R 33/54; G01R 33/543; G01R 33/561; G01R 33/563; G01R 33/565; G01R 33/5612; G01R 33/583; G01R 33/5659; G01R 33/56518; G01R 33/56572; G01R 33/5611; G01R 33/5614; G01R 33/5616; G01R 33/56509; G01R 33/341; G01R 33/385; G01R 33/56358
See application file for complete search history.

(56) References Cited

U.S. PATENT DOCUMENTS

| | | | | |
|---|---|---|---|---|
| 4,899,108 A * | 2/1990 | Fujita | ............... | G01R 33/34069 |
| | | | | 324/318 |
| 5,585,721 A * | 12/1996 | Datsikas | .......... | G01R 33/34046 |
| | | | | 324/318 |
| 6,169,399 B1 * | 1/2001 | Zhang | ................. | G01R 33/341 |
| | | | | 324/309 |
| 6,300,761 B1 * | 10/2001 | Hagen | .................... | A61B 5/055 |
| | | | | 324/318 |
| 7,772,842 B2 | 8/2010 | Gao et al. | | |
| 8,030,930 B2 * | 10/2011 | Li | .................... | G01R 33/34046 |
| | | | | 324/322 |
| 9,081,070 B2 * | 7/2015 | Konijn | ............... | G01R 33/3875 |
| 2002/0089329 A1 * | 7/2002 | Harvey | ............. | G01R 33/3415 |
| | | | | 324/309 |
| 2005/0104591 A1 * | 5/2005 | Qu | ..................... | G01R 33/3415 |
| | | | | 324/318 |
| 2012/0146667 A1 | 6/2012 | Syms et al. | | |

FOREIGN PATENT DOCUMENTS

| | | | |
|---|---|---|---|
| JP | 2016511095 | A | 4/2016 |
| KR | 20000069263 | A | 11/2000 |
| KR | 100416947 | B1 | 1/2004 |
| KR | 20050106062 | A | 11/2005 |
| KR | 20100011118 | A | 2/2010 |

OTHER PUBLICATIONS

Blasiak, Barbara et al., "An RF Breast Coil for 0.2T MRI", Concepts in Magnetic Resonance Part B, vol. 46B(1) 3-7 (2016).

De Perrot, Thomas et al., "Potential of hybrid 18F-fluorocholine PET/MRI for prostate cancer imaging", Eur J Nucl Med Mol Imaging (2014) 41:1744-1755, Received: Jan. 9, 2014 /Accepted: Apr. 15, 2014 /Published online: May 20, 2014 Springer-Verlag Berlin Heidelberg 2014.

Delso, Gaspar et al., "MR-driven metal artifact reduction in PET/CT", Physics in Medicine and Biology 58 (2013) 2267-2280, IOP Publishing.

Difilippo, Frank P. et al., "Do Implanted Pacemaker Leads and ICD Leads Cause Metal-Related Artifact in Cardiac PET/CT?", The Journal of Nuclear Medicine • vol. 46 • No. 3 • Mar. 2005.

Groheux, David et al., "Performance of FDG PET/CT in the Clinical Management of Breast Cancer", Radiology: vol. 266: No. 2: pp. 388-405—Feb. 2013.

Hendrick, Edward, "High-Quality Breast MRI", Radiol Clin N Am 52 (2014) 547-562.

MacDonald, Lawrence R., et al., "Effects of MR surface coils on PET quantification", Medical Physics, vol. 38, No. 6, Jun. 2011.

Moy, Linda et al., "Prone MammoPET Acquisition Improves the Ability to Fuse MRI and PET Breast Scans", Clinical Nuclear Medicine • vol. 32, No. 3, pp. 194-198, Mar. 2007.

Zhang, Shaomin et al., "Defining PET tumor volume in cervical cancer with hybrid PET/MRI: a comparative study", Nuclear Medicine Communications 2014, 35:712-719.

* cited by examiner

RADIO FREQUENCY COIL AND MEDICAL IMAGING DEVICE INCLUDING SAME

TECHNICAL FIELD

The present disclosure relates to a radiofrequency coil and a medical imaging device including the same, and more specifically, a radiofrequency coil which is used to photograph the human body using a magnetic field and a medical imaging device including the same

BACKGROUND

Recently, various diagnostic imaging devices to diagnose the body for prevention and treatment of diseases, such as a magnetic resonance imaging (hereinafter, MRI) device using a magnetic field generated by a magnetic force, a positron emission tomography (hereinafter, PET) device that detects gamma rays derived from a radioactive tracer, a computed tomography (hereinafter, CT) device that uses an X-ray generator, e.g. are widely used.

The MRI device used to determine the internal structure of a subject includes a transmit-and-receive radiofrequency coil (RF coil) that can receive and transmit radiofrequency (RF) signals so as to acquire images from an electromagnetic field. For optimal images, it is desirable that the radiofrequency coil be designed according to the body part of the human body, and the shape and the studies on the pattern of the radiofrequency coil to obtain the maximum signal-to-noise ratio (SNR) are underway.

Such an MRI device provides excellent anatomical information through excellent soft tissue contrast and high spatial resolution, but the device has limitations in providing information on body metabolism of living organisms. Meanwhile, the PET device, which can obtain physiochemical and functional images of the human body in three dimensions using radiopharmaceuticals, provides information on body metabolism of living organisms, but in reality the device lacks spatial resolution.

Considering these points, studies on MRI/PET are in progress to visualize disease cells that proliferate in soft tissues by fusion of these two kinds of images, and there has been much progress with respect to imaging of the whole body and the head.

Meanwhile, recently, the use of an MRI device for breasts has been rapidly increasing, and there is a growing interest in fusion images of MRI and PET. However, in order to photograph the images of breasts, a subject needs to be in a prone position, and when the subject is such a position is taken, the radiofrequency coil dedicated to the breast becomes very close to the breast tissue. When the breast-specific radiofrequency coil is located very close to the breast tissue, the coil can cause image distortion and thus it is difficult to apply a conventional radiofrequency coil to MRI/PET or PET/CT.

Additionally, positrons can cause beam-hardening artifact due to hardening at the soldering site of the radiofrequency coil thereby severely distorting the image information.

PRIOR ART DOCUMENTS

Patent Documents (Patent Document 1) KR Patent Application Publication No. 2010-0011118 (Feb. 3, 2010)

DISCLOSURE

Technical Problem

An embodiment of the present inventive concept provides a radiofrequency coil that can minimize the image distortion due to a beam-hardening artifact, and a medical imaging device including the same.

An embodiment of the present inventive concept provides a radiofrequency coil for mammography that can minimize the image distortion due to a beam-hardening artifact, and a medical imaging device including the same.

Additionally, an embodiment of the present inventive concept provides MRI, CT, PET, and MRI/PET, each of which includes a radiofrequency coil that can minimize the image distortion due to a beam-hardening artifact.

Technical Solution

In an embodiment of the present inventive concept, the medical radiofrequency coil may include a base substrate; and a radio coil unit, which includes: a first coil element that has a rectangular shape and is formed along an edge of the inner circumference of the base substrate; and a second coil element that is formed at the inner side of the first coil element and has a shape of paired paddles connected to each other.

The second coil element may include paddle units, which are symmetrical to each other; and a connecting unit which connects the paddle units, which are symmetrical to each other.

The paddle unit may have a rectangular shape or the paddle unit may have an oval shape.

The radio coil unit may be included in a radiofrequency coil for mammography.

The base substrate may have a cylindrical shape.

The medical radiofrequency coil may include a joining unit which joins the first coil element and the second coil element together, and the joining unit may include a conductive paint.

Another embodiment of the present inventive concept provides an imaging device including a medical radiofrequency coil, in which the medical radiofrequency coil includes: a base substrate; and a radio coil unit including: a first coil element, which has a rectangular shape and is formed along an edge of the inner circumference of the base substrate; and a second coil element, which is formed at the inner side of the first coil element and has a shape of paired paddles connected to each other.

The imaging device may be selected from a group comprising an MRI device, a CT device, a PET device, and an integrated device for MRI/PET.

Advantageous Effects

According to an embodiment of the present inventive concept, there is provided a radiofrequency coil that can minimize the image distortion due to a beam-hardening artifact, and a medical imaging device including the same.

According to another embodiment of the present inventive concept, there is provided a radiofrequency coil for mammography that can minimize the image distortion due to a beam-hardening artifact, and a medical imaging device including the same.

Additionally, according to another embodiment of the present inventive concept, there are provided MRI, CT, PET, and MRI/PET, each of which includes a radiofrequency coil that can minimize the image distortion due to a beam-hardening artifact.

MODE FOR INVENTION

Figure 1:
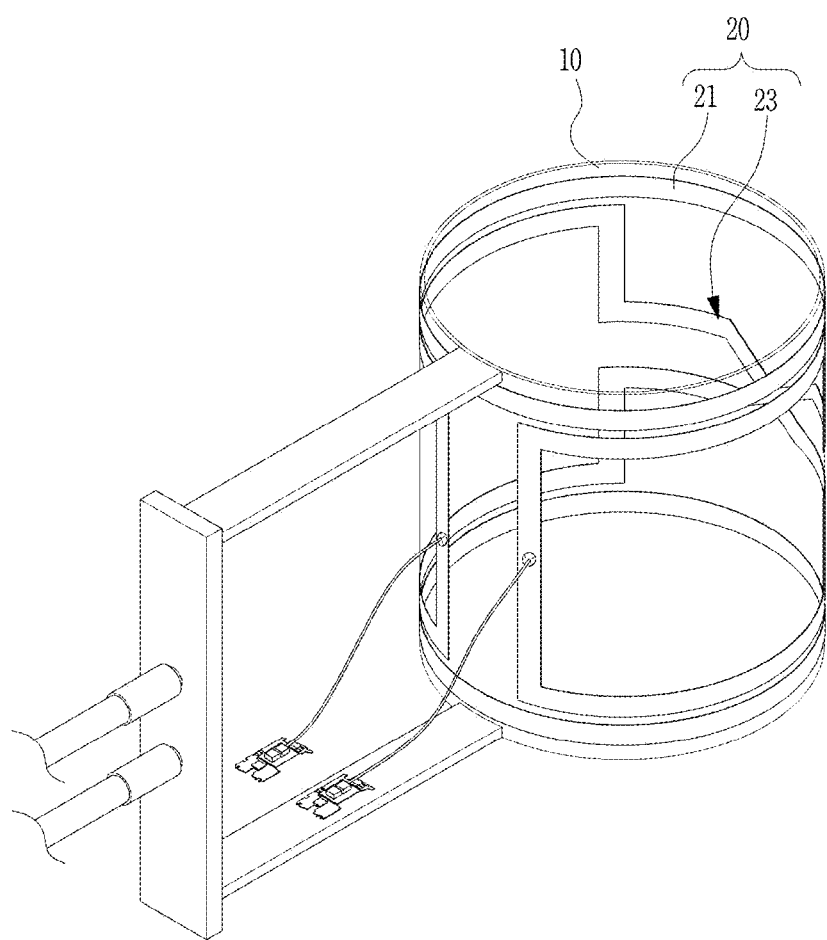
FIG. 1 is a schematic diagram of a radio frequency coil according to an embodiment of the present inventive concept.

Hereinafter, embodiments of the present inventive concept will be described in detail with reference to the accompanying drawings so that those skilled in the art can easily carry out the present inventive concept. However, the present inventive concept may be embodied in many different forms and is not limited to the embodiments set forth herein. In order to clearly illustrate the present inventive concept, parts not related to the description are omitted, and like reference numerals designate like elements throughout the specification.

In the present specification, duplicate descriptions are omitted for the same constituent elements.

Further, in the present specification, when it is described that a constituent element is "connected" or "electrically connected" to another constituent element, it should be understood that the element may be "directly connected" or "directly electrically connected" to the other constituent elements or may be "connected" or "electrically connected" to the other constituent elements through a third element. However, in the present specification, when it is described that a constituent element is "directly connected" or "directly electrically connected" to another constituent element, it should be understood that no element may exist between the element and the other constituent elements.

Further, terms used in the present specification are used for describing a specific embodiment and do not limit the present inventive concept.

Further, in the present specification, unless the context otherwise clearly indicates, words used in the singular include the plural, and the plural includes the singular.

Further, in the present specification, a term "comprise" or "have" indicates presence of a characteristic, numeral, step, operation, element, component, or combination thereof described in the specification and does not exclude presence or addition of at least one other characteristic, numeral, step, operation, element, component, or combination thereof.

Further, in the present specification, a term "and/or" includes a combination of a plurality of described items or any item of a plurality of described items. In this specification, 'A or B' may include 'A', 'B', or 'both A and B'.

Hereinafter, embodiments of the present inventive concept will be described in detail with reference to the drawings. In the following description of the embodiments of the present inventive concept, detailed description of related known configurations or functions will be omitted when it is determined that they may make the subject matter of the present disclosure rather unclear.

It is to be understood that the description of "including" a specific configuration in the present inventive concept does not exclude a configuration other than the configuration, and that additional configurations may be included in the practice of the present inventive concept or the technical scope of the present inventive concept.

In the present inventive concept, the subject may be a person, an animal or a part of a person or an animal. For example, the subject may include organs such as the liver, heart, brain, uterus, breast, abdomen, e.g. or blood vessels. In addition, the subject may include small animals such as laboratory mice, companion animals such as dogs and cats, large animals such as cows and horses, e.g. In addition, the "subject" may include phantom. A phantom refers to a material which has a volume very close to the density and the effective atomic number of a bioorganism, and the subject may include a spherical or cylindrical phantom with properties of the body.

In addition, as used herein, the term "user" may refer to a physician, a radiologist, a nurse, a clinical pathologist, a medical imaging expert, e.g., and may also refer to a technician repairing medical devices, but the user is not limited thereto.

In addition, as used herein, the term "magnetic resonance imaging (MRI)" refers to an image of a subject obtained using the nuclear magnetic resonance principle, and it includes magnetic resonance arthrography and magnetic resonance angiography.

The MRI device is a device capable of photographing a cross-section of a subject using a nuclear magnetic resonance phenomenon. The MRI device employs a technique based on the principle that atomic nuclei such as hydrogen, phosphorus, sodium, carbon isotopes, e.g. existing in the human body have inherent rotational field constants due to nuclear magnetic resonance, in which, a human body is inserted into a large magnet barrel that generates a strong magnetic field, and then a radio frequency (RF) is generated to resonate the magnetization vector of the hydrogen nuclei in the body region, and the differences in magnetic resonance signals (electromagnetic waves) from each tissue are measured and reconstituted for generation of imaging using a computer. In particular, radio frequency (RF) coils are used to apply electromagnetic waves (transmit mode, transmit) in the human body so as to resonate the magnetization vectors in the human body, and to receive signals due to resonance (receive mode, receive).

These radio frequency coils may be used as a transmit-and-receive coil that performs both transmission and reception with one coil, or they may be used with two or more coils as to separately function transmission and reception modes. In addition, the radiofrequency coil may be divided into a body type coil installed in the external device of an MRI device, and a surface type or volume type coil attached to or placed adjacent to a subject. The body-type coil may be mounted on a cylindrical or oval-shaped frame sized to accommodate the subject, and the surface-type or volume-type coil may be prepared in a detachable form according to the form of the attachment site of the subject such as a head coil, a neck coil, a waist coil, a breast coil, or a table on which the subject is placed. Such a radiofrequency coil must be designed according to the area to be applied so as to obtain the maximum signal-to-noise ratio (SNR).

Figure 2:
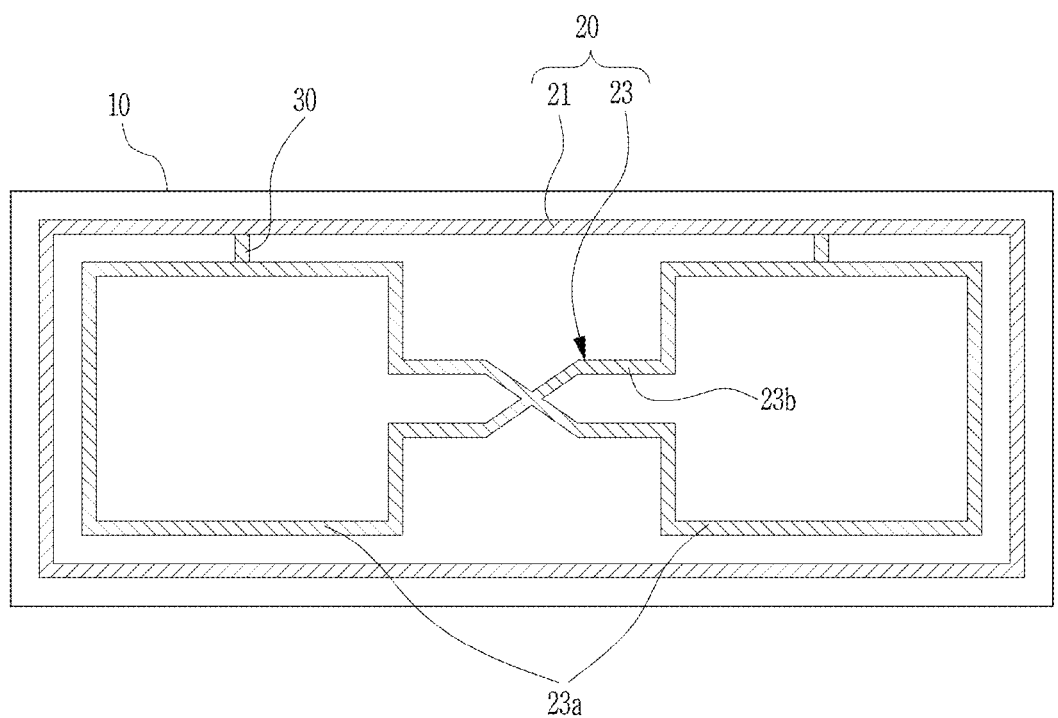
FIG. 2 is a plan view of the radio frequency coil according to FIG. 1.

FIG. 1 is a schematic diagram of a radio frequency coil according to an embodiment of the present inventive concept; and FIG. 2 is a plan view of the radio frequency coil according to FIG. 1. Hereinafter, the shape and the pattern of the radio frequency coil according to the present inventive concept will be described with reference to FIGS. 1 and 2.

The radiofrequency coil according to this embodiment may include a base substrate 10, a radio coil unit 20, and a joining unit 30.

For the base substrate 10, any plate which is provided with a coil and is of any material and shape commonly used may be used. As shown in FIG. 1, the base substrate 10 according to the present embodiment may have a cylindrical shape. Since the base substrate 10 has a cylindrical shape, it is suitable for high-resolution images of the breast. That is, by positioning a subject's breast on the base substrate 10 with a cylindrical shape, high-resolution imaging of the breast is possible, and specifically, the base substrate 10 is expected to be useful for the examination of Asians whose breasts are smaller than those of Westerners.

The base substrate 10 may preferably be a substrate for forming by coating a coil or may be a substrate for holding and supporting a coil only. Such fixation may include physical fixation of the coil to the substrate with a tape or adhesive; or a bonding that is electrically conductive by means of solder, a conductive paint, e.g.; or a combined form thereof.

More preferably, the base substrate 10 may be in the form of a PCB substrate, a plastic substrate, a metal substrate, a resin substrate, or a film.

A radio coil unit 20 may include a radio coil unit which includes a first coil element 21 that has a rectangular shape and is formed along an edge of the inner circumference of a base substrate 10; and a second coil element 23 that is formed at the inner side of the first coil element 21 and has a shape of paired paddles connected to each other.

As illustrated in FIG. 2, the shapes of the first coil element 21 and the second coil element 23 formed on the base substrate 10 can be more easily confirmed by spreading the base substrate 10 with a cylinder shape in a planar manner. In FIG. 2, it can be seen that both ends of the base substrate 10 are connected with each other.

As illustrated, the first coil element 21 and the second coil element 23 are formed along the inner circumference of the base substrate 10, and the first coil element 21 and the second coil element 23 are arranged on a single base substrate 10 rather than on base substrates which are different from each other.

According to the present inventive concept, the second coil element 23 is formed in the shape of paddles which are connected with each other as a pair as described above, that is, they are formed in the shape of a row. The second coil element 23 may include paddle units 23a, which are symmetrical to each other, and a connecting unit 23b that connects the paddle units 23a, which are symmetrical to each other. In the case of the radiofrequency coil according to this embodiment, such a paddle-shaped pattern is optimized for mammography. Additionally, due to the paddle shape, the second coil element 23 is advantageous in acquiring medical images even for a large-sized breast because the second coil element 23 can cover a wider range of the body compared to the conventional loop coil. That is, the radiofrequency coil according to this embodiment may be used as a volumetric coil applicable to a radiofrequency coil for mammography. Alternatively, the radiofrequency coil may also be used to minimize image distortion even when the subject needs to be in a prone position for photographing.

As illustrated in FIGS. 1 and 2, the paddle units 23a may be in a square shape formed along the first coil element 21, or may be in an oval or other polygonal shapes according to other embodiments. The shape of the paddle units 23a may be modified differently depending on the structure and size of the body, and an imaging device in which the radiofrequency coil is used.

That is, the main feature of the present inventive concept lies in that the shape of the radiofrequency coil has a paddle shape to be suitable for a particular body part as in mammography, and the paddle shape may be variously modified for optimal image uniformity and/or SNR.

The radiofrequency coil according to the present inventive concept can control its shape according to the shape of the site where the radiofrequency coil is to be used. As described above, the radiofrequency coil according to an embodiment of the present inventive concept may be a volumetric coil used for MRI, PET, and/or MRI/PET for breasts, and thus the overall shape may be a circular or oval shape, but the present inventive concept is not limited thereto. The radiofrequency coil elements arranged within a radiofrequency coil unit may be composed of those with a different shape and size from one another.

In addition, the radiofrequency coil according to an embodiment of the present embodiment may be a coil which functions the role of any one selected from the group consisting of a static magnetic field coil for forming a static magnetic field for a subject, a gradient magnetic field coil for forming a gradient magnetic field for a subject, a transmission coil for inducing a magnetic resonance phenomenon in a subject by applying electromagnetic waves to the subject on which the static magnetic field and the gradient magnetic field are formed, a receiving coil for receiving a magnetic resonance signal generated according to the induced magnetic resonance phenomenon, and a composite coil performing one or more of the above roles.

More preferably, the radiofrequency coil may be any one selected from the group consisting of a transmission coil for inducing a magnetic resonance signal, a receiving coil for receiving a magnetic resonance signal, and a transmit-and-receive coil for performing both transmission and reception in a complex manner.

As illustrated in FIG. 2, the radiofrequency coil may include a joining unit 30 which joins the first coil element 21 and the second coil element 23 together.

The joining unit 30 may serve to attach a radio coil unit 20 to the base substrate 10 as well as to connect the first coil element 21 and the second coil element 23. The joining unit 30 may be a part which simultaneously performs the connection of the coil elements and the attachment of a substrate, or may be a part where the connection of the coil elements and the attachment of the substrate are each performed separately.

The joining unit 30 according to the present embodiment may include a conductive paint. The joining unit 30 may contain 0.1-100 wt % of a conductive paint. When the joining unit 30 contains less than 0.1 wt % of a conductive paint, a beam-hardening artifact may be observed in photographing of an imaging device (e.g., MRI, CT, PET, e.g.).

Additionally, the joining unit 30 may further contain one or more compositions that can be used in conventional joining units, such as conventional adhesives for improving adhesiveness, solvents for adjusting concentrations, thickeners, e.g. in addition to the conductive paint.

Figure 3:
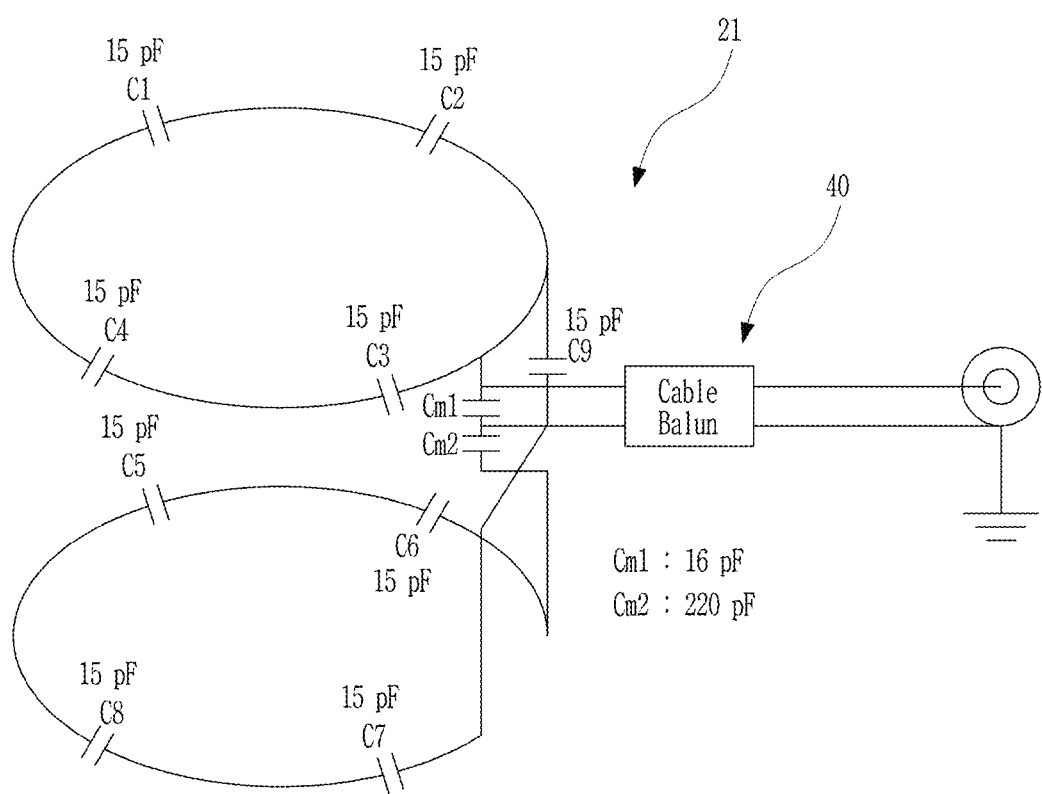
FIG. 3 is a circuit diagram of a first coil element according to FIG. 1.
Figure 4:
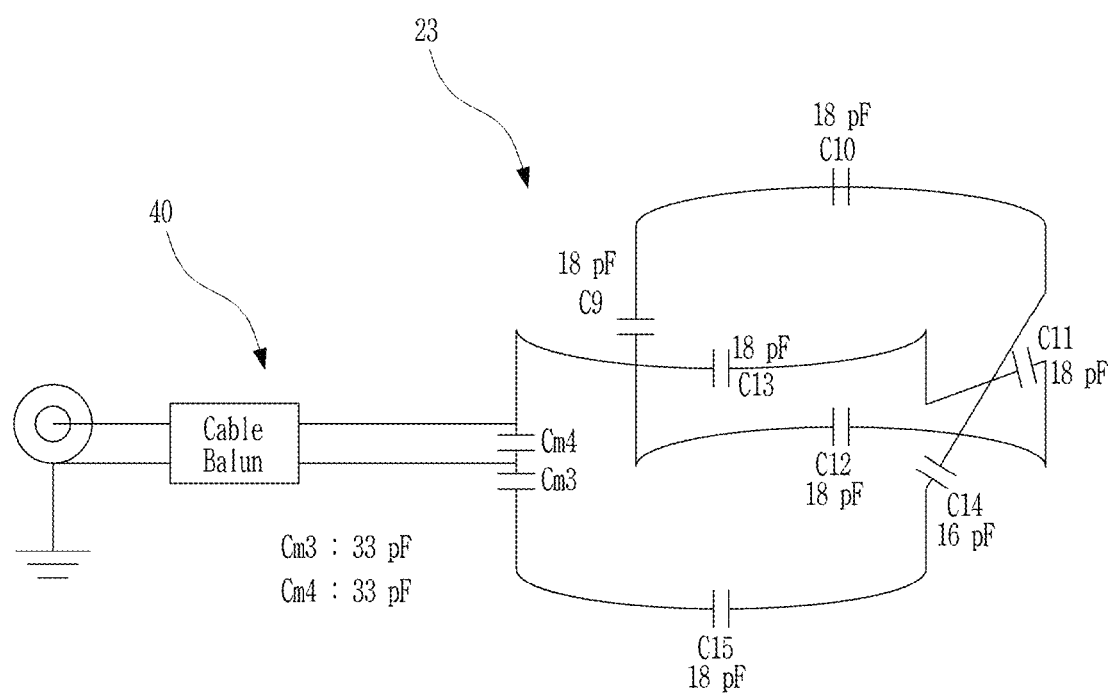
FIG. 4 is a circuit diagram of a second coil element according to FIG. 1.

FIG. 3 is a circuit diagram of a first coil element according to FIG. 1; and FIG. 4 is a circuit diagram of a second coil element according to FIG. 1.

The radiofrequency coil may further include a cable balun 40, which is connected to each of the first coil element 21 and the second coil element 23, as illustrated in FIGS. 3 and 4.

The first coil element 21 may be formed in a cylindrical shape along the inner circumference of the base substrate 10 and may include a plurality of capacitors.

The second coil element 23 may also include a plurality of capacitors, and the capacitance of the capacitors illustrated is not limited to the value shown as an example.

Among the plurality of capacitors, both ends of Cm1 in FIG. 3 and Cm4 in FIG. 4 are respectively connected to the coaxial cable via the cable balun 40.

Figure 5:
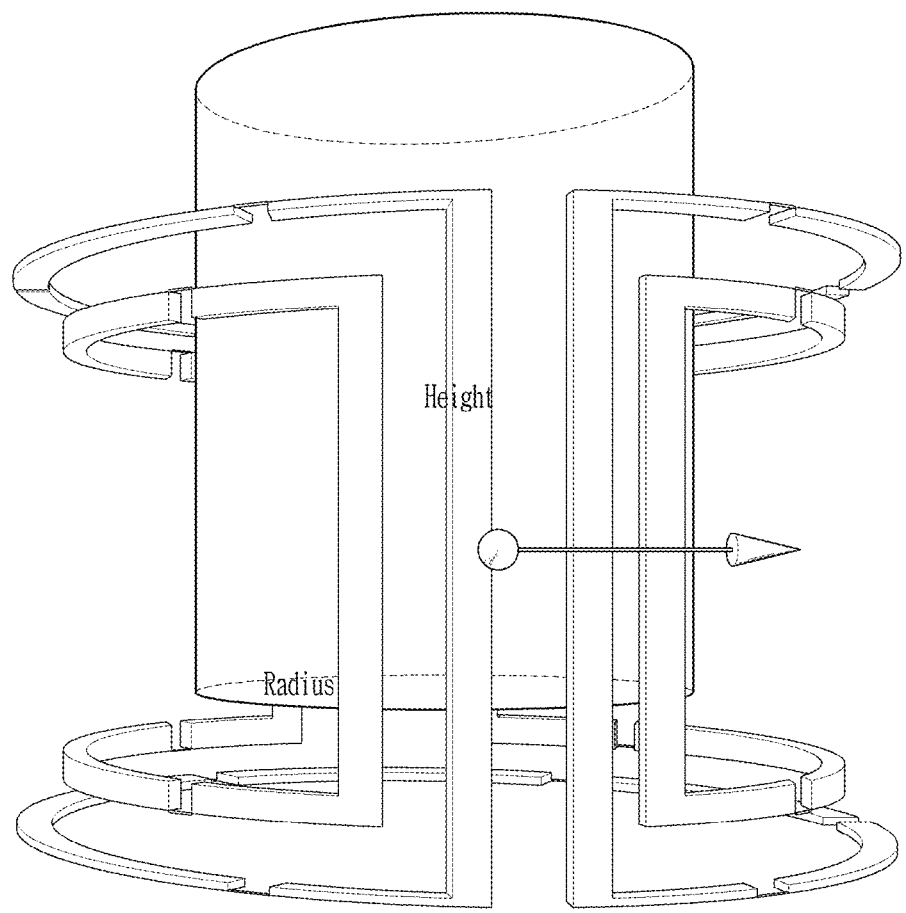
FIG. 5 is a view illustrating a coil pattern and a phantom for simulating a coil according to an embodiment of the present inventive concept.

FIG. 5 is a view illustrating a coil pattern and a phantom for simulating a coil according to an embodiment of the present inventive concept; and FIGS. 6 to 11 are diagrams for explaining a magnetic field simulation performed on the phantom of FIG. 5.

The radiofrequency coil in FIG. 5 is one where a copper tracer is wound at 127.7 MHz, and 14 capacitors are distributed on the coil elements. Among the coil elements used in the radio frequency coil, the top and bottom coils corresponding to the first coil element are saddle loop type coils, and the side coils corresponding to a second coil element are also composed of saddle loop type coils.

The top and bottom coils have an inner diameter of 150 mm and a height of 90 mm, and the copper tracer has a thickness of 5 mm. The inner diameter of the side coil and the thickness of the copper tracer are 150 mm and 5 mm, respectively, as in the top and bottom coils, and the height is 75 mm.

The dielectric phantom located inside the radiofrequency coil has a height of 100 mm, a diameter of 80 mm, a relative permittivity of 87.699, and an electric conductivity of 0.66264 S/m. The dielectric phantom is located about 35 mm above the bottom of the radiofrequency coil.

FIGS. 6 to 11 illustrate the uniformity and the specific absorption rate (SAR) of a magnetic field examined by applying a magnetic field to the dielectric phantom.

Figure 6:
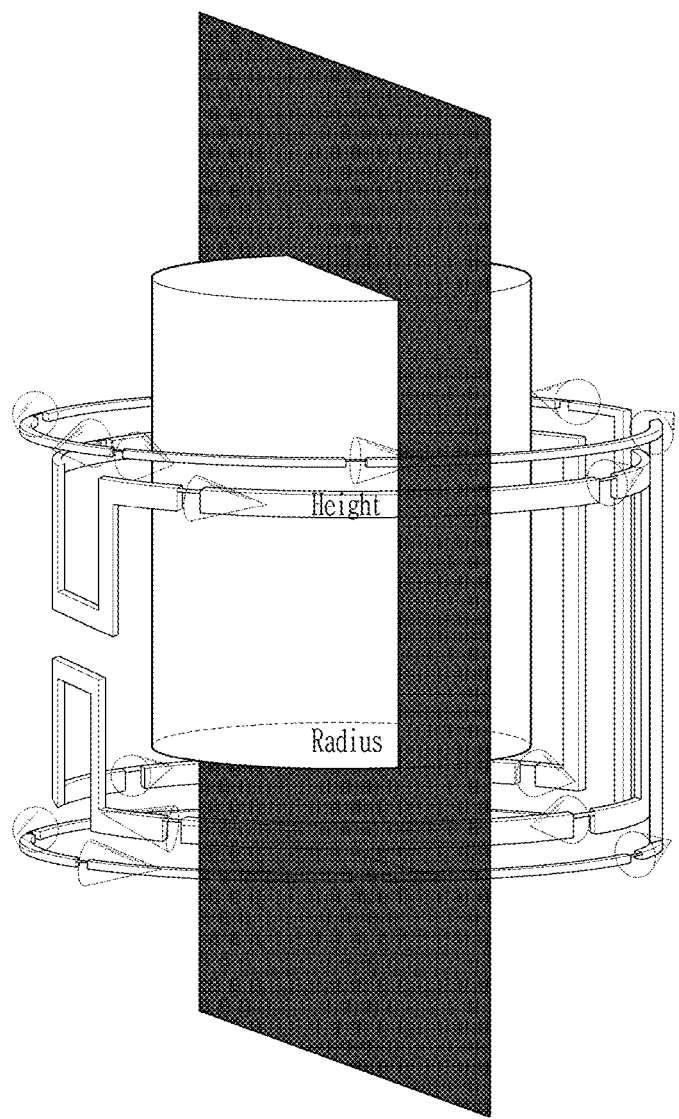
FIG. 6, FIG. 7, and FIG. 8 are diagrams for explaining a magnetic field simulation performed on the phantom of FIG. 5.
Figure 7:
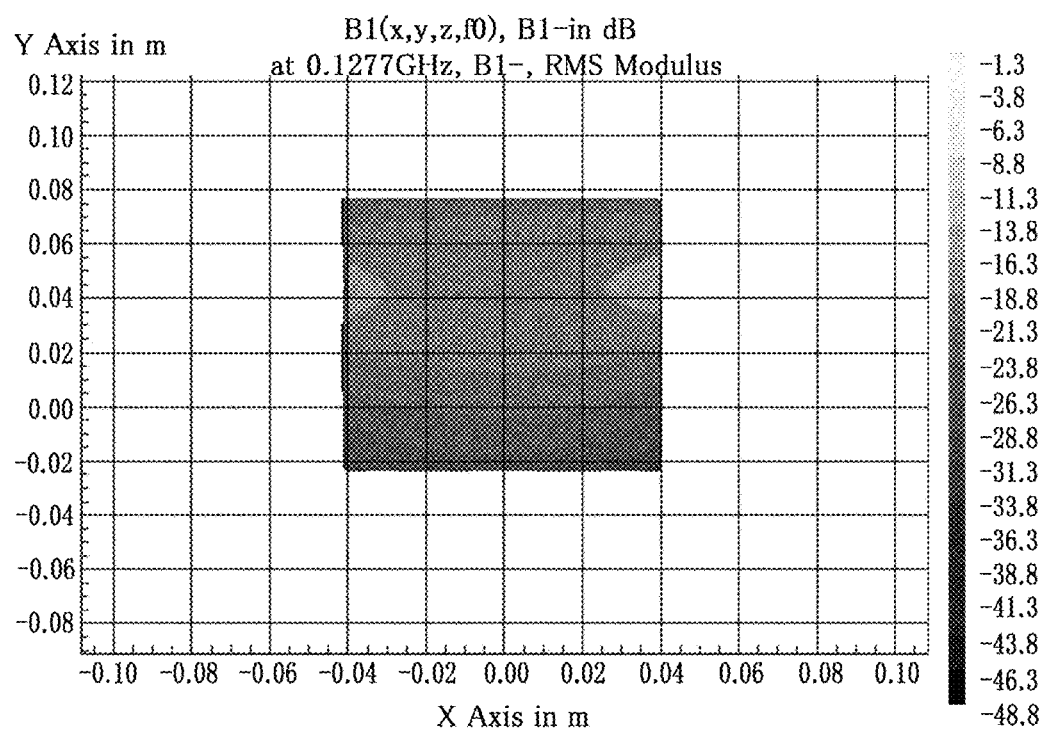
Figure 8:
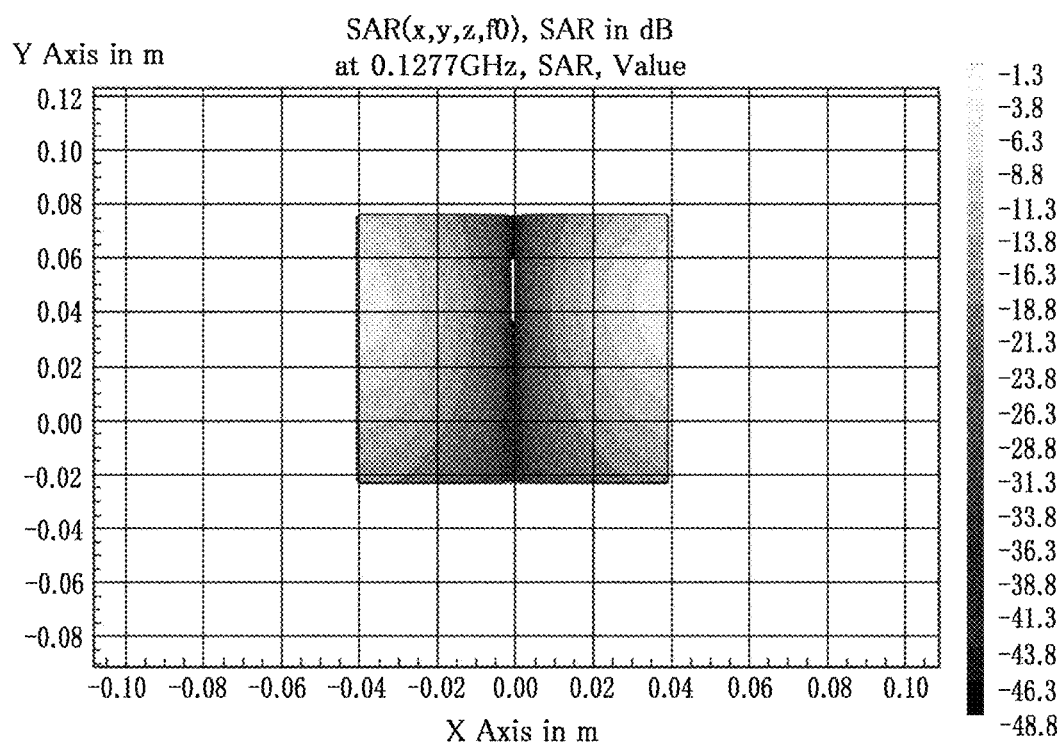
Figure 9:
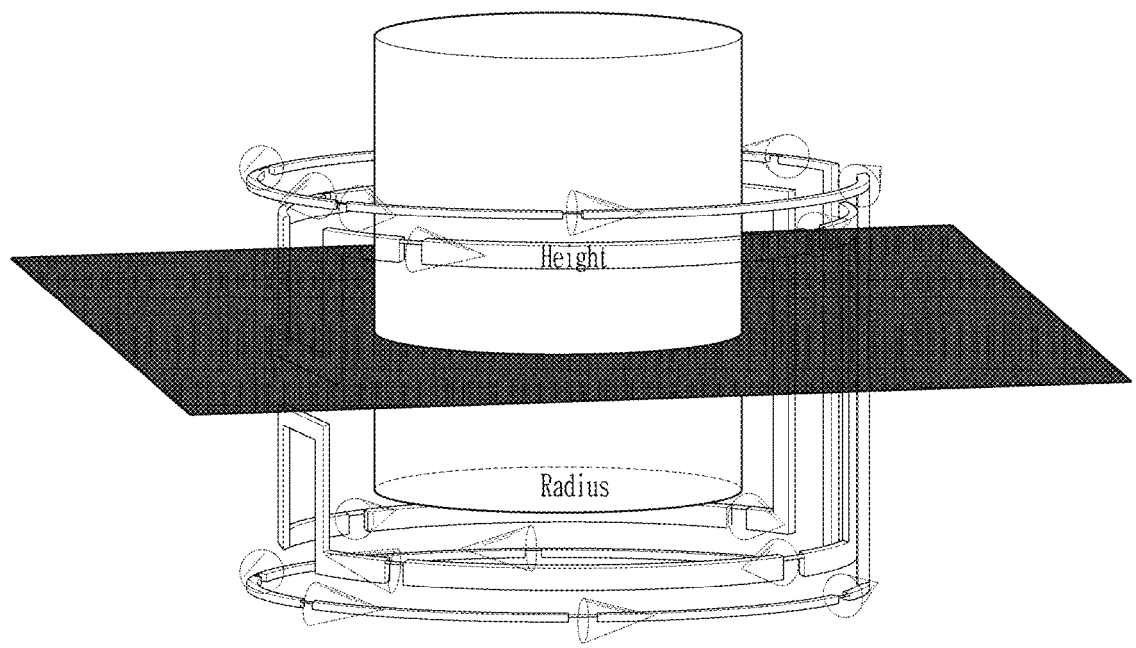
FIG. 9, FIG. 10, and FIG. 11 are other diagrams for explaining a magnetic field simulation performed on the phantom of FIG. 5.
Figure 10:
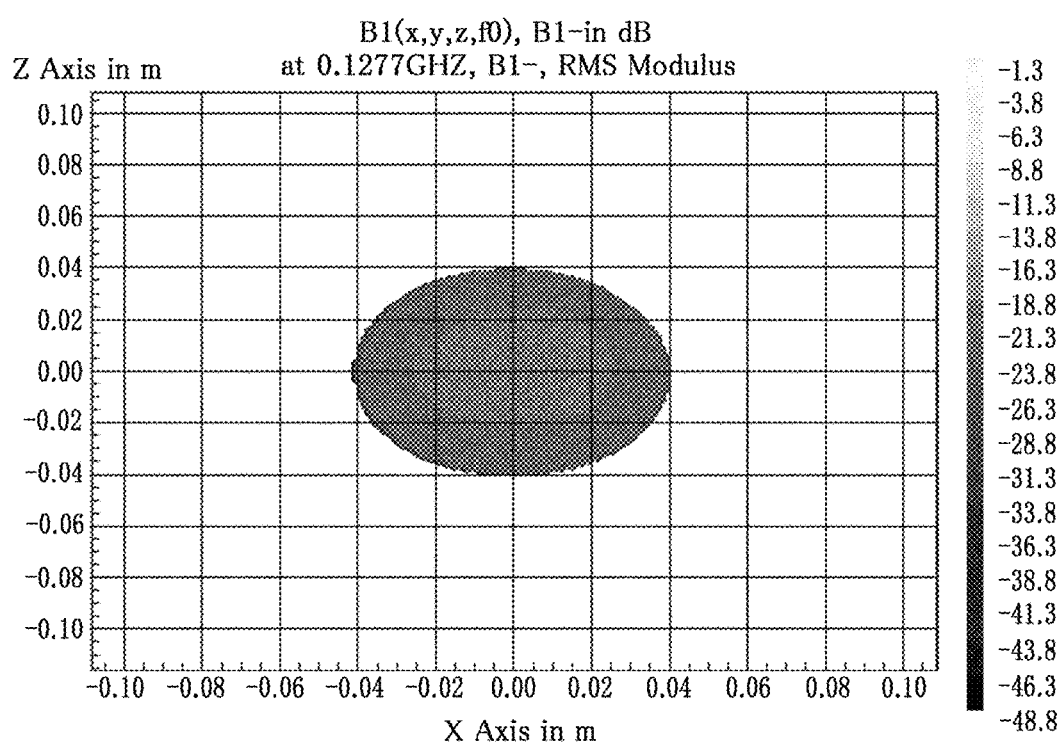
Figure 11:
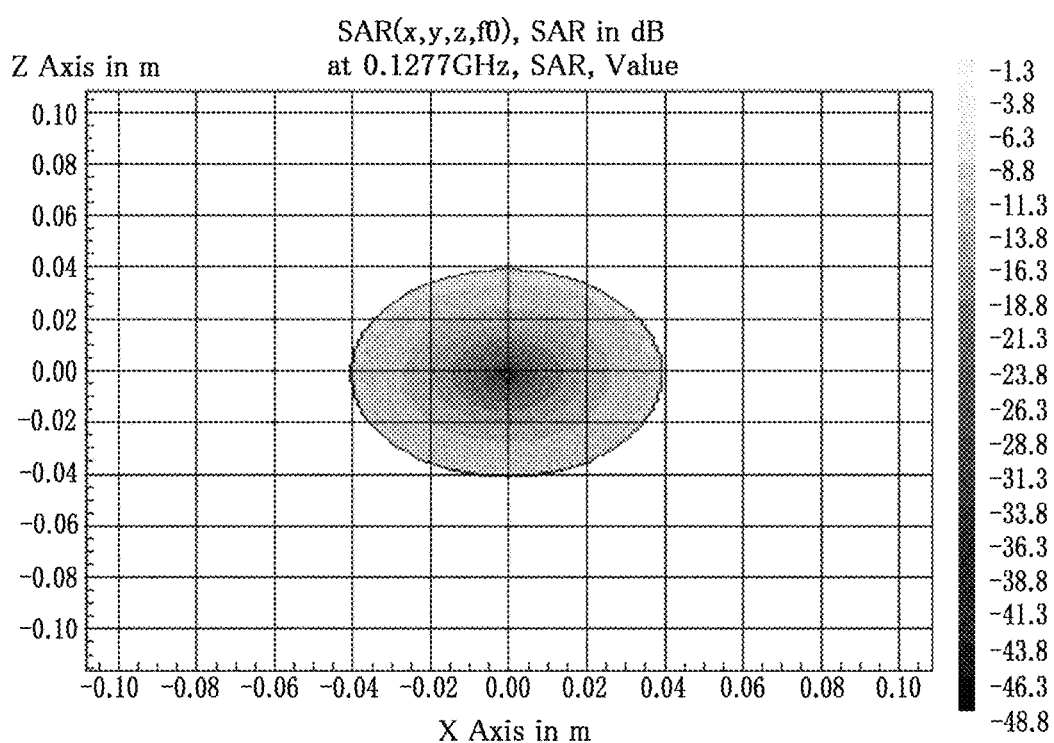

As illustrated, FIGS. 6 to 8 are diagrams illustrating simulation results from the vertical direction, i.e., in the axial direction, in a case where a magnetic field is applied to the phantom of FIG. 5; and FIGS. 9 to 11 are diagrams illustrating simulation results from a horizontal direction, i.e., when viewed from a coronal plane where the breasts are located in a case where a magnetic field is applied to the phantom of FIG. 5.

As illustrated, in the vertical and horizontal directions of the phantom, it is confirmed that the magnetic field, i.e., B1 field (Normalized $5 \times 10^{-13}$ V/m² as 0.0 dB) will be observed to be nearly uniform and the SAR (Normalized $1.0 \times 10^{-14}$ W/kg as 0.0 dB), which means the absorption rate of electromagnetic energy in living tissue with energy absorbed by mass per unit time, will not be very high. This means that the radiofrequency coil according to the present inventive concept effectively contributes to the uniformity of the B1 magnetic field and is designed such that the energy of a magnetic field generated by the coils is not absorbed to the human body.

Figure 12:
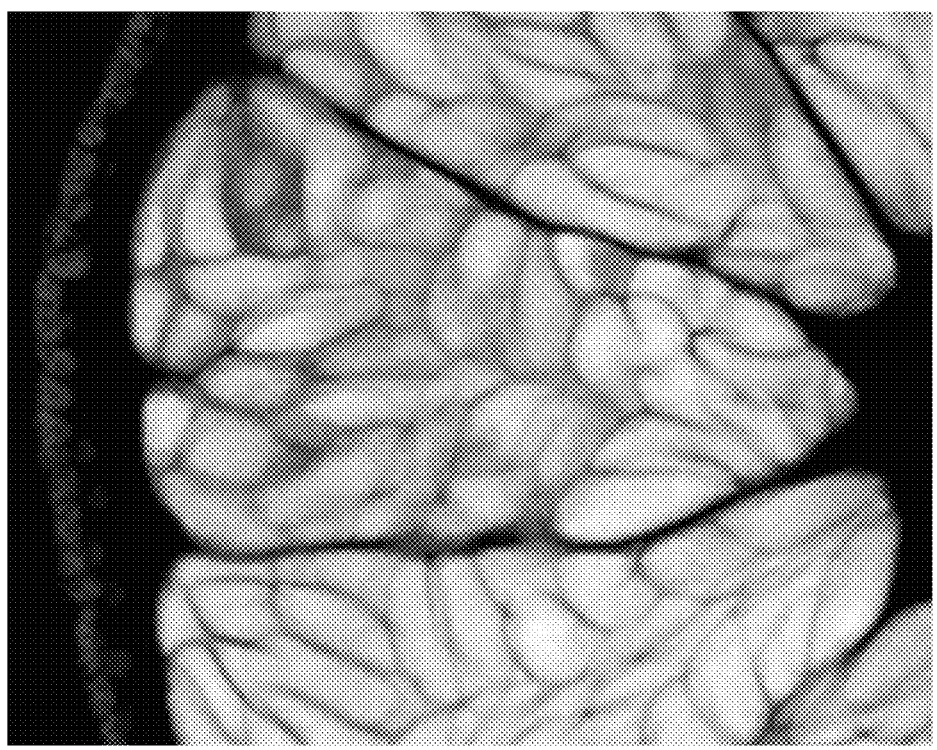
FIGS. 12 and 13 are comparative photographs illustrating MRI image evaluation of a radiofrequency coil according to an embodiment of the present inventive concept.
Figure 13:
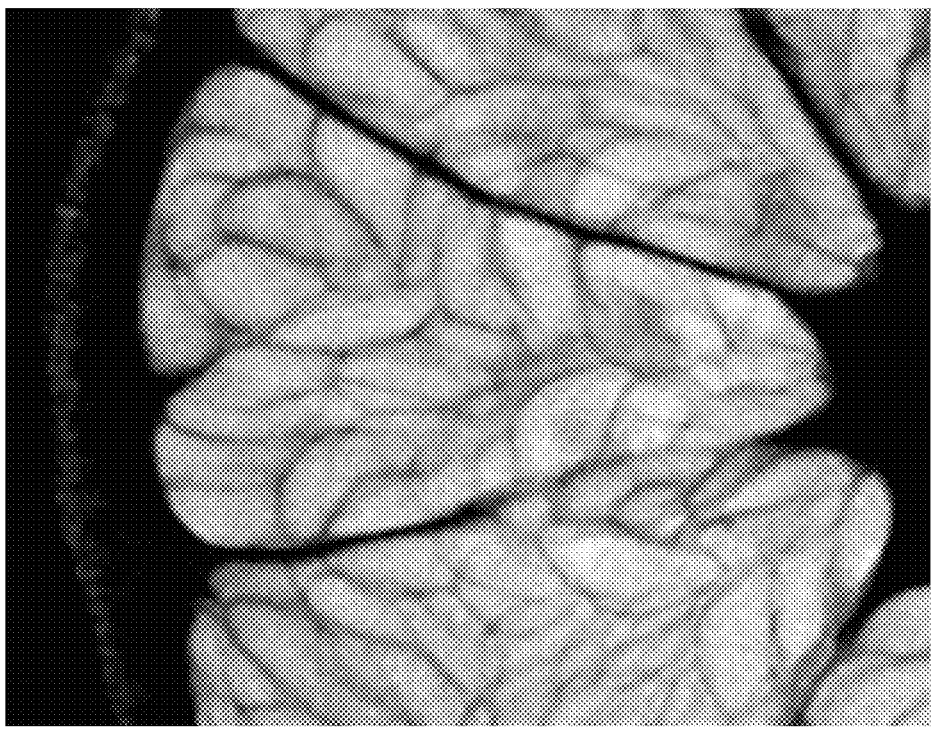

FIGS. 12 and 13 are comparative photographs of MRI image evaluation of a radiofrequency coil according to an embodiment of the present inventive concept. FIG. 12 shows an MRI evaluation result of a radio frequency coil according to an embodiment of the present inventive concept as shown in FIG. 1, and FIG. 13 shows an MRI evaluation result of a conventional radio frequency coil.

The coil of FIG. 1 prepared for image evaluation was connected to a 3T clinical scanner (Discovery MR750, GE Healthcare, Waukesha, Wis., USA), and as the loading phantom, a bottle having a diameter of 115 mm and a height of 240 mm used in image quality control was used (IN-VIVO, Pewaukee, Wis. USA). The interior of the bottle consisted of 2.0±0.05 g/L $CuSO_4$-$5H_2O$, 4.5±0.05 g/L NaCl, and 1.89 L distilled water.

It is possible to evaluate the appropriateness of the images by calculating the integral uniformity (IU) and the SNR within the viewing angle from the images obtained by the MRI as shown in FIGS. 12 and 13. As illustrated, in the case of the radiofrequency coil of FIG. 1, the SNR is high and the image is clear and the overall uniformity of the image is observed to be high compared with conventional radio frequency coils.

Figure 14:
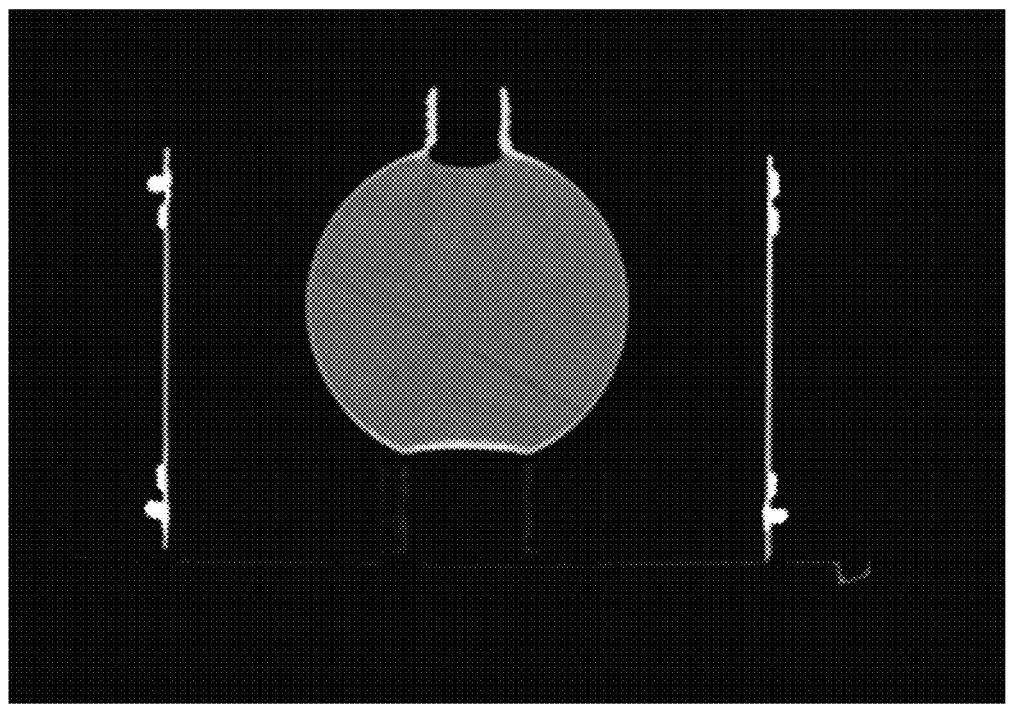
FIGS. 14 and 15 are comparative photographs of CT image evaluation of a radiofrequency coil according to an embodiment of the present inventive concept.
Figure 15:
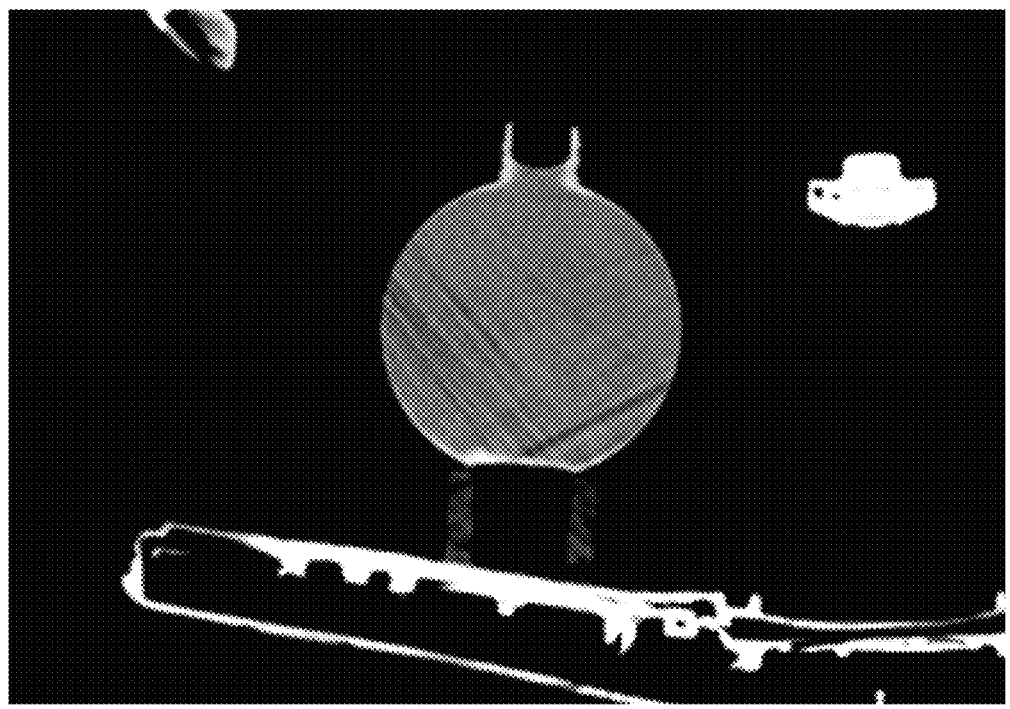

FIGS. 14 and 15 are comparative photographs illustrating CT image evaluation of a radiofrequency coil according to an embodiment of the present inventive concept. FIG. 14 shows a CT evaluation result of a radio frequency coil according to an embodiment of the present inventive concept, and FIG. 15 shows a CT evaluation result of a conventional radio frequency coil.

Images were obtained from a clinical CT imager (Sensation 64, Siemens Healthcare, Erlangen, Germany) for the evaluation of beam-hardening artifact with regard to PET/CT by applying a radiofrequency coil according to the present inventive concept and a conventional radiofrequency coil. The parameters used in the image were 120 kVp, 72 mA, a slice thickness of 5 mm, and an image recon algorithm of B41f.

CT images were photographed using the radiofrequency coil according to the present inventive concept and the conventional radiofrequency coil, respectively, and the results of beam-hardening artifact were evaluated by two professional radiologists as consensus and shown in FIGS. 14 and 15.

As shown in FIGS. 14 and 15, in the CT image evaluation performed by the two professional radiologists, no noticeable artifact phenomenon was observed in the radiofrequency coil according to the present inventive concept, unlike the conventional radiofrequency coil.

However, in the conventional radiofrequency coils used in the past, image distortion due to soldering and electronic devices, i.e., the artifact phenomenon was observed.

When these radiofrequency coils are used for mammograms of real patients, it is expected that the anatomic information by MRI and the metabolic image information by PET can be obtained at the same time, thereby significantly contributing to imaging diagnosis.

As described above, the radiofrequency coil according to the present embodiment can be applied to all of MRI, CT, and PET imaging devices, and in addition, the radiofrequency coil has an effect that the artifact beam-hardening does not appear even in a prone position as in mammogram. That is, the radiofrequency coil according to the present inventive concept can be used for an imaging device selected from the group consisting of an MRI device, a CT device, a PET device, and an integrated device for MRI/PET.

As described above, according to the present inventive concept, a radiofrequency coil capable of minimizing image distortion due to a beam-hardening artifact and a medical imaging device including the same can be provided.

The present inventive concept provides a radiofrequency coil and a medical imaging device including the same. The radiofrequency coil and the medical imaging device can minimize image distortion due to beam-hardening artifact.

A computing device according to an embodiment of the present inventive concept may be, for example, the device described in the present specification. The computing device may include at least one processor and a memory. Further, the computing device may further include a transceiver, a storage device, an input interface device, and an output interface device. Components included in the computing device may be connected by a bus and communicate with each other. The processor may execute a program command stored in at least one of the memory and the storage device. The processor may mean a central processing unit (CPU), a graphics processing unit (GPU), or a dedicated processor on which methods according to embodiments of the present inventive concept are performed. The processor may be configured to implement procedures, functions, methods, and the like described in connection with the embodiments of the present inventive concept. The processor may control each component of the computing device. Each of the memory and the storage device may store various information related to an operation of the processor. Each of the memory and the storage device may be configured with at least one of a volatile storage medium and a non-volatile storage medium. For example, the memory may be configured with at least one of a read only memory (ROM) and a random access memory (RAM). The transceiver (transmitting and receiving device) may transmit or receive a wired signal or a wireless signal. The transceiver may be connected to a network to perform communication.

The above-described embodiments can be realized through a program for realizing functions corresponding to the configuration of the embodiments or a recording medium for recording the program in addition to through the above-described device and/or method, which is easily realized by a person skilled in the art.

The above-described embodiments include examples of various aspects. While it is not possible to describe every possible combination for expressing various aspects, one of ordinary skill in the art will recognize that other combinations are also possible. Accordingly, the invention is expected to include all such alternatives, modifications, and variations that fall within the scope of the following claims.

The invention claimed is:

1. A medical radiofrequency coil, comprising:
   a base substrate;
   a radio coil unit comprising:
      a first coil element, which has a rectangular shape and is formed along an edge of an inner circumference of the base substrate; and
      a second coil element, which is formed at an inner side of the first coil element and has a shape of paired paddles connected to each other; and
   a joining unit attaching the radio coil unit to the base substrate and electrically connecting the first coil element and the second coil element.

2. The medical radiofrequency coil of claim 1, wherein the second coil element comprises paddle units, which are symmetrical to each other; and a connecting unit that connects the paddle units, which are symmetrical to each other.

3. The medical radiofrequency coil of claim 2, wherein the paddle units have a rectangular shape.

4. The medical radiofrequency coil of claim 2, wherein the paddle units have an oval shape.

5. The medical radiofrequency coil of claim 1, wherein the radio coil unit is comprised in a radiofrequency coil for mammography.

6. The medical radiofrequency coil of claim 1, wherein the base substrate has a cylindrical shape.

7. The medical radiofrequency coil of claim 1, wherein the joining unit comprises a conductive paint.

8. The medical radiofrequency coil of claim 1, wherein the medical radiofrequency coil is characterized in that applied to any device selected from a group comprising a magnetic resonance imaging (MRI) device, a computed tomography (CT) device, a positron emission tomography (PET) device, and an integrated device for magnetic resonance imaging (MRI)/positron emission tomography (PET).

9. The medical radiofrequency coil of claim 1, wherein the first coil element surrounds the second coil element so as to be between the edge and the second coil element.

10. The medical radiofrequency coil of claim 1, wherein the first coil element is formed in a cylindrical shape.

11. The medical radiofrequency coil of claim 1, wherein the first coil element includes a plurality of capacitors.

* * * * *